(12) United States Patent
Fischer et al.

(10) Patent No.: US 9,050,081 B2
(45) Date of Patent: Jun. 9, 2015

(54) ANTI-CARBONIZATION DEVICE

(75) Inventors: Klaus Fischer, Nagold (DE); Alexander Neugebauer, Moessingen (DE); Markus Enderle, Tuebingen (DE); Matthias Zenker, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 463 days.

(21) Appl. No.: 13/395,394

(22) PCT Filed: Sep. 7, 2010

(86) PCT No.: PCT/EP2010/005485
§ 371 (c)(1),
(2), (4) Date: Mar. 9, 2012

(87) PCT Pub. No.: WO2011/029573
PCT Pub. Date: Mar. 17, 2011

(65) Prior Publication Data
US 2012/0172789 A1  Jul. 5, 2012

(30) Foreign Application Priority Data

Sep. 11, 2009 (DE) .......... 10 2009 041 168
Nov. 12, 2009 (DE) .......... 10 2009 044 512

(51) Int. Cl.
*A61B 18/18* (2006.01)
*A61B 18/04* (2006.01)
*A61B 18/00* (2006.01)

(52) U.S. Cl.
CPC ..... *A61B 18/042* (2013.01); *A61B 2018/00583* (2013.01)

(58) Field of Classification Search
CPC ............... A61B 2018/00601; A61B 18/042; A61B 18/00589
USPC .................................. 606/49, 40
See application file for complete search history.

(56) References Cited

U.S. PATENT DOCUMENTS

| 6,582,427 B1 | 6/2003 | Goble et al. |
| 2003/0153908 A1 | 8/2003 | Goble et al. |
| 2004/0116918 A1 | 6/2004 | Konesky |
| 2005/0118350 A1 | 6/2005 | Koulik et al. |
| 2007/0029500 A1 | 2/2007 | Coulombe et al. |
| 2009/0039790 A1 | 2/2009 | Suslov |
| 2010/0114092 A1* | 5/2010 | Eisele et al. ............ 606/41 |
| 2011/0139751 A1* | 6/2011 | Koo et al. ............ 216/67 |

FOREIGN PATENT DOCUMENTS

| CN | 101170958 A | 4/2008 |
| DE | 195 16 238 A1 | 11/1996 |
| DE | 697 18 466 T2 | 11/2003 |
| DE | 699 17 073 T2 | 4/2005 |
| DE | 10 2007 025 551 A1 | 12/2008 |
| EP | 0 740 926 A2 | 11/1996 |

(Continued)

*Primary Examiner* — Christopher D Koharski
*Assistant Examiner* — Philip Edwards
(74) *Attorney, Agent, or Firm* — Dickstein Shapiro LLP

(57) ABSTRACT

An anti carbonization device to prevent the carbonization of tissue upon plasma coagulation by a suitable surgical instrument, wherein the surgical instrument has a feed line for an oxidizing agent, a feed line for a gas and an electrode for generating a plasma. A gas-oxidizing agent mixture for generating a gas oxidizing agent plasma is provided by the anti-carbonization device.

10 Claims, 6 Drawing Sheets

(56) References Cited

FOREIGN PATENT DOCUMENTS

| | | |
|---|---|---|
| EP | 1 829 492 A1 | 9/2007 |
| EP | 2 160 081 A1 | 3/2010 |
| JP | 2008-543355 A | 12/2008 |
| RU | 2 161 931 C2 | 1/2001 |
| RU | 2 195 226 C2 | 12/2002 |
| WO | WO 2006/119892 A1 | 11/2006 |
| WO | WO 2008/090004 A1 | 7/2008 |
| WO | WO 2009/060213 A1 | 5/2009 |
| WO | WO 2009/146432 A1 | 12/2009 |

* cited by examiner

ANTI-CARBONIZATION DEVICE

FIELD OF THE INVENTION

The invention relates to an anti-carbonization device to prevent the carbonization of tissue upon plasma coagulation.

BACKGROUND

High-frequency (HF) surgery, of which argon plasma coagulation is a subset, has been used for many years, both in human medicine and in veterinary medicine, to coagulate and/or cut biological tissue. Suitable electrosurgical instruments are used to pass high-frequency current through the tissue to be treated, so that this tissue changes as a result of protein coagulation and dehydration. Vessels can be sealed and bleeding stopped through this coagulation process. A cutting process that follows the coagulation process then enables full separation of tissue that has already coagulated.

Argon plasma coagulation enables a non-contact coagulation of tissue and serves for effective haemostasis and devitalization of tissue. In this type of coagulation, inert working gas, for example argon, is passed via gas supply devices from an argon plasma coagulation instrument to the tissue to be treated. With the help of the working gas, a "plasma jet" can be generated between an electrode at a distal end of the gas supply device, such as a probe, and the tissue. The HF current can then be applied to the tissue to be treated without the electrosurgical instrument coming into contact with the tissue. This, therefore, avoids adherence of the tissue to the instrument.

An undesirable side effect of plasma coagulation, in particular argon plasma coagulation, is the carbonization of the tissue that is seen in virtually all electrosurgical applications. Plasma coagulation is accompanied by a chemically incomplete combustion of the biological tissue which results in carbonization of the tissue to a substantial degree and to the formation of carbon black and plume formation. These disadvantages are seen with argon plasma coagulation to a lesser degree than with laser surgery procedures, but carbonization results, and is accompanied by increased tissue inflammation and increased post-operative problems. The use of higher power and longer application times in argon plasma surgery leads to significant carbonization and therefore emission of carbon black and plumes that are harmful to health and have a strong odor. This necessitates expensive and complicated extraction devices and cleaning of the operating room. A further disadvantage of plasma coagulation is that relatively inhomogeneous tissue damage is seen, caused by the concentrated development of current paths of the noble gas plasma. This produces depressions on the tissue surface, which are carbonized to a greater degree at higher power levels and longer application times than the rest of the tissue surface.

SUMMARY

An aim of the embodiments of the invention is therefore to provide an anti-carbonization device that avoids carbonization of tissue during plasma coagulation and also ensures a more homogeneous tissue treatment.

The aim is achieved through an anti-carbonization device that serves to prevent carbonization of tissue upon plasma coagulation, wherein the plasma coagulation is performed by means of a suitable surgical instrument. The surgical instrument has a feed line for an oxidizing agent, a feed line for a gas and an electrode for generating a plasma. Furthermore, the anti-carbonization device provides a gas-oxidizing agent mixture for producing a gas-oxidizing agent plasma. The gas-oxidizing agent mixture can be ignited by a high-frequency alternating electric field between the electrode and the tissue to be treated, so that a plasma is generated, which contains the introduced gas on the one hand and the oxidizing agent on the other. The supply of an oxidizing agent to the gas results in cooling of the tissue surface, thereby advantageously reducing carbonization of the tissue. In addition, the oxidizing agent oxidizes the carbon that is formed during the plasma coagulation, thereby causing a reduced development of carbon black and plumes. In principle, all substances that can oxidize carbon are suitable as an oxidizing agent. Furthermore, it is particularly advantageous for the plasma energy to be more uniformly distributed over the entire coagulation surface by the entry of the oxidizing agent. Moreover, the anti-carbonization device proposed herein substantially reduces dehydration (desiccation) of the tissue surface. With increasing application time, there is consequently a markedly lower drop in electrical impedance of the biological tissue, which allows longer medically-relevant treatment times than are possible with conventional plasma coagulation.

Particularly preferred is an embodiment of the anti-carbonization device, wherein the oxidizing agent is liquid or gaseous. The oxidizing agent is preferably water and the gas is an inert gas, particularly argon. The oxidizing agent may also be in the form of an aerosol, so that it is atomized into fine droplets of the oxidizing agent to form an oxidizing agent mist. The oxidizing agent mist increases the specific surface area and thus the heat exchange area between the oxidizing agent and the carrier gas by more than a hundredfold, so that the evaporation point of the liquid oxidizing agent droplets is substantially reduced and the oxidizing agent mist therefore evaporates more rapidly. As a result, a substantial proportion of the oxidizing agent is also present as oxidizing agent vapor. This allows a proportion of the oxidizing agent, namely that portion in the form of a gas, to be ionized to an oxidizing agent vapor plasma. A reactive plasma is formed in this process, which in the case of water as the oxidizing agent contains species such as $H_2O^+$, H, OH and O radicals. By increasing the specific surface area, the tissue surface can, moreover, be cooled markedly, which reduces carbonization. It is also conceivable to convert the oxidizing agent prior to provision of the gas-oxidizing agent mixture into its gaseous state using an evaporator. Furthermore, nanoparticles with particular properties can be mixed into the oxidizing agent, for instance to intensify or accelerate a therapeutic effect or reduce side-effects. It is conceivable, for example, to mix in nanoparticles that have a positive effect on the wound healing process.

Further preferred is an embodiment of the anti-carbonization device wherein the surgical instrument to generate the aerosol has an evaporator. Furthermore, instead of an evaporator, an ultrasound generating device can be provided to generate the aerosol. Alternatively, however, a baffle may be provided, against which the oxidizing agent impacts, so that it is atomized upon rebounding from the surface. In this manner, the gas-oxidizing agent mixture can be provided in a particularly simple way by the anti-carbonization device.

An embodiment of an anti-carbonization device is also preferred, which is characterized in that at least one two-substance atomization device/two-substance nozzle is provided. This may have internal or external mixing. With the two-substance atomization device it is possible in a simple manner to provide a gas-oxidizing agent mixture for generation of a gas-oxidizing agent plasma.

Finally, an embodiment of an anti-carbonization device is preferred, which is characterized in that the surgical instrument has a hose which in the area of the electrode has at least one opening to prevent a gas embolism. At least the probability of a gas embolism or the development of emphysema in contact with the tissue is thereby substantially reduced.

Furthermore, a self-aspirating two-substance atomization device can be provided, which is preferably created by the arrangement of the gas supply channel and the oxidizing agent supply channel and which makes an additional pump for the supply of the oxidizing agent unnecessary.

The aim of the embodiments of the present invention is also achieved by a method to prevent the carbonization of tissue upon plasma coagulation. The surgical instrument preferably has a feed line for an oxidizing agent, a feed line for a gas and an electrode to generate a plasma. The method is characterized by provisioning a gas-oxidizing agent mixture to generate a gas-oxidizing agent plasma. The advantageous method described herein enables carbonization of the tissue to be substantially reduced, since the carbon formed is oxidized by the oxidizing agent. In addition, the surface of the tissue is cooled by the oxidizing agent at the same time. Especially preferred is an oxidizing agent which is liquid or gaseous. However, the oxidizing agent may also be in the form of an aerosol. In this case, the surgical instrument preferably has a corresponding device for generation of the aerosol. The oxidizing agent must be suitable to oxidize carbon, which is the case, for example, with water. The gas is preferably an inert gas, especially argon.

The aim of the embodiments of the invention is lastly achieved through the use of an anti-carbonization device according that provides a gas-oxidizing agent mixture for generation of a gas-oxidizing agent plasma, resulting in an advantageous reduction in the carbonization of the tissue.

BRIEF DESCRIPTION OF THE DRAWINGS

Hereinafter, exemplary embodiments of the invention are explained in greater detail with reference to drawings, in which.

DETAILED DESCRIPTION

Figure 1:
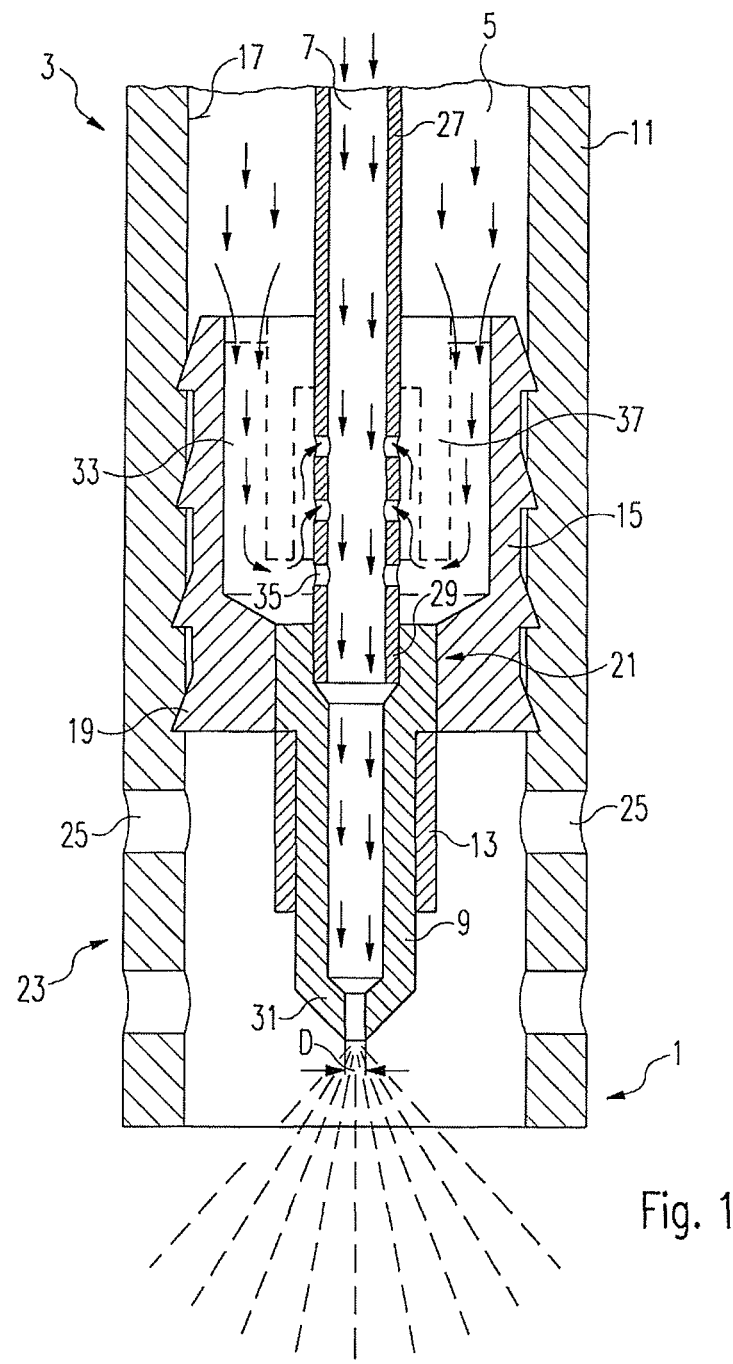
FIG. 1 is a schematic sectional view of a first embodiment of an anti-carbonization device.

FIG. 1 shows a schematic sectional view of a first embodiment of an anti-carbonization device 1 according to the present disclosure. The device 1 serves to reduce carbonization of tissue upon plasma coagulation, preferably to prevent it entirely, wherein the plasma coagulation is performed a suitable surgical instrument 3.

The surgical instrument 3 has a supply line 5 for a gas, hereinafter referred to as gas supply channel 5, and a supply line 7 for an oxidizing agent, hereinafter referred to as oxidizing agent supply channel 7. Furthermore, an electrode/electrode tip 9 is provided, which is connected to a high-frequency voltage source, not shown, that supplies high-frequency current to the electrode tip 9. The electrode tip 9 is otherwise hollow and thus quasi forms an extension of the oxidizing agent supply channel 7.

The gas supply channel 5, the oxidizing agent supply channel 7 and the electrode 9 of FIG. 1 are arranged by way of example within a hose 11, which is preferably constructed of PTFE and is connected to an HF surgical instrument, not shown.

FIG. 1 clearly shows that a protective insulation 13 is provided, which coaxially envelops the electrode tip 9 at least in part. Furthermore, a fixing sleeve 15 is provided inside the hose 11, and is secured to the inner wall 17 of the hose 11 by suitable locking projections 19 and envelops the electrode tip 9 in a distal region 21.

The distal end 23 of the hose 11 that envelops the electrode tip 9 has, moreover, lateral openings 25 through which the gas-oxidizing agent mixture can escape, so that a gas embolism and emphysema development can be avoided when the distal end 23 of the hose 11 comes into contact with the tissue.

The oxidizing agent supply channel 7 is formed in a pipe 27, which is preferably of stainless steel, in particular V2A steel. The pipe 27 is connected at a proximal end, not shown, to a HF voltage source and thus simultaneously serves as an electrical conductor, which supplies the electrode tip 9 with a high-frequency current. For this purpose, the distal end 29 of the pipe 27 is connected to the electrode tip 9.

Furthermore, the pipe 27 is connected to an oxidizing agent source, not shown, so that an oxidizing agent can pass through the pipe 27 and through the electrode tip 9 to a distal end 31 of the electrode tip 9.

FIG. 1 clearly shows that an annular space 33 is provided between the fixing sleeve 15 and the pipe 27 into which gas from the gas supply channel 5 is passed. Furthermore, the pipe 27 in the region of the annular space 33 has at least one opening, a plurality of openings 35 are illustrated, through which the gas can flow from the annular space 33 into the oxidizing agent supply channel 7. Furthermore, a diffuser 37 can be arranged in the annular space 33 and is shown by dashed lines in FIG. 1.

The gas supply channel 5 and the oxidizing agent supply channel 7 of the surgical instrument 3 thus together form a two-substance nozzle, which is an internal-mixing type, so that the gas and the oxidizing agent are fed separately to a mixing chamber, wherein the mixing chamber in the present embodiment is formed by the oxidizing agent supply channel 7. Only after mixing is the gas-oxidizing agent mixture passed through a nozzle to the outside, the nozzle being formed by the distal end 31 of the electrode tip 9. The distal end 31 may for this purpose have a specific inner diameter D and a suitable shape to produce a desired jet width of the ejected gas-oxidizing agent mixture.

In this way, the gas-oxidizing agent mixture is atomized upon exiting the oxidizing agent supply channel 7 so that the oxidizing agent/gas-oxidizing agent mixture is present as an aerosol. To perform plasma coagulation, the electrode tip 9 is brought close to the tissue to be treated and the escaping atomized gas-oxidizing agent mixture is ignited by the electrode tip 9/high-frequency current applied there, so that a conductive gas-oxidizing agent plasma results between the tissue surface and the electrode tip 9 through which the high-frequency current can flow from the electrode tip 9 to the tissue to bring about coagulation of the tissue at that point.

The above-described anti-carbonization device 1 is particularly preferably used for argon plasma coagulation. Argon is therefore preferably used as the gas and is supplied to the oxidizing agent through the gas supply channel 5, the annular space 33 and the openings 35. Any substance that is suitable for the oxidation of carbon can be used as the oxidizing agent. However, water is preferably used as the oxidizing agent and oxidizes carbon formed upon plasma coagulation according to the following formula:

$$131.38 \text{ kJ/mol} + C + H_2O(g) \rightarrow CO + H_2 \tag{1}$$

$$CO + H_2O(g) \rightarrow CO_2 + H_2 + 41.19 \text{ kJ/mol} \tag{2}$$

$$90.19 \text{ kJ/mol} + C + 2H_2O(g) \rightarrow CO_2 + 2H_2 \tag{3}$$

The oxidizing agent can be fed in liquid or gaseous form into the oxidizing agent supply channel 7. If the oxidizing agent is fed in liquid form into the oxidizing agent supply channel 7 it is preferably provided that the oxidizing agent is converted by a suitable mechanism into an aerosol. The oxidizing agent can also be converted into the respective gaseous substance, wherein the gaseous oxidizing agent is generated in advance, for example using an evaporator.

In the embodiment shown in FIG. 1, for example, the oxidizing agent is fed in liquid form through the oxidizing agent supply channel 7 and is mixed with the gas from the gas supply channel 5. The gas-oxidizing agent mixture is then fed to the nozzle in the distal end 31 of the electrode tip 9. In this way, the gas-oxidizing agent mixture is atomized so that it is in the form of an aerosol after emerging from the electrode, where it is ignited by the HF current to a plasma. A gas-oxidizing agent plasma thus results.

Studies have shown in this context, moreover, that the presence of a fine oxidizing agent mist, in particular a water mist, results in a better ignition of the gas-oxidizing agent mixture.

The oxidizing agent is used to generate a gas-oxidizing agent plasma, as described above, preferably atomized into fine droplets, as a result of which the specific surface area of the oxidizing agent is substantially increased. At the same time, this results in a substantial depression of the evaporation point of the oxidizing agent, so that a part of the oxidizing agent in the plasma is converted into its gaseous state more rapidly. The gaseous part can then be ionized by the existing gas plasma to an oxidizing agent vapor plasma and thereby contributes to the conduction of the current from the electrode to the tissue surface. The ignition of the gaseous oxidizing agent is supported by the plasma already present, in particular by an argon plasma. As a result of the atomization of the oxidizing agent/gas-oxidizing agent mixture at least a part of the oxidizing agent serves as plasma medium.

The gas-oxidizing agent plasma thus contains the ionized gas, atomized oxidizing agent, i.e., small droplets of oxidizing agent and ionized oxidizing agent. If argon is used as carrier gas and water as the oxidizing agent, a plasma results from the above-described, which has positively-charged argon cations, positively-charged water vapor radical cations and radical species such as H, OH and O.

Overall, the provision of a gas-oxidizing agent mixture yields the following advantages:

The atomized gas-oxidizing agent mixture has an increased specific surface area, so that the oxidizing agent droplets cool the tissue surface during plasma coagulation. This results in a reduction of the carbonization of the tissue.

Furthermore, the increase in the specific surface area leads to a lowering of the evaporation point of the oxidizing agent, so that at least a part of the vaporized oxidizing agent evaporates (i.e., is in gas form). The gaseous part can then be ionized by the alternating electric field and forms a conductive oxidizing agent vapor plasma. The high-frequency alternating current that is passed through the conductive plasma is responsible for the origin of Joule heat energy in the course of work to be performed upon entry into the biological tissue, which in turn, as a side effect, leads to heating of the biological tissue with the corresponding desired therapeutic effect. The oxidizing agent therefore contributes in its ionized state to the therapeutic effect.

Finally, the oxidizing agent, in particular the liquid oxidizing agent droplets in the plasma, oxidizes the carbon that forms during carbonization, as a result of which the carbonization and the emission of carbon black and smoke can be reduced.

Overall, it should be noted therefore that the gas-oxidizing agent mixture is preferably present as an aerosol, wherein the gas is mixed with the atomized oxidizing agent. In this way, the oxidizing agent serves at the same time as a coolant for the tissue surface, as an oxidizing agent for carbon and as plasma medium for the conduction of high-frequency current from the electrode tip 9 to the tissue.

In addition, the use of the present anti-carbonization device 1 brings about a more uniform distribution of the plasma energy over the coagulation area, so that concentrated current paths are avoided.

Figure 2:
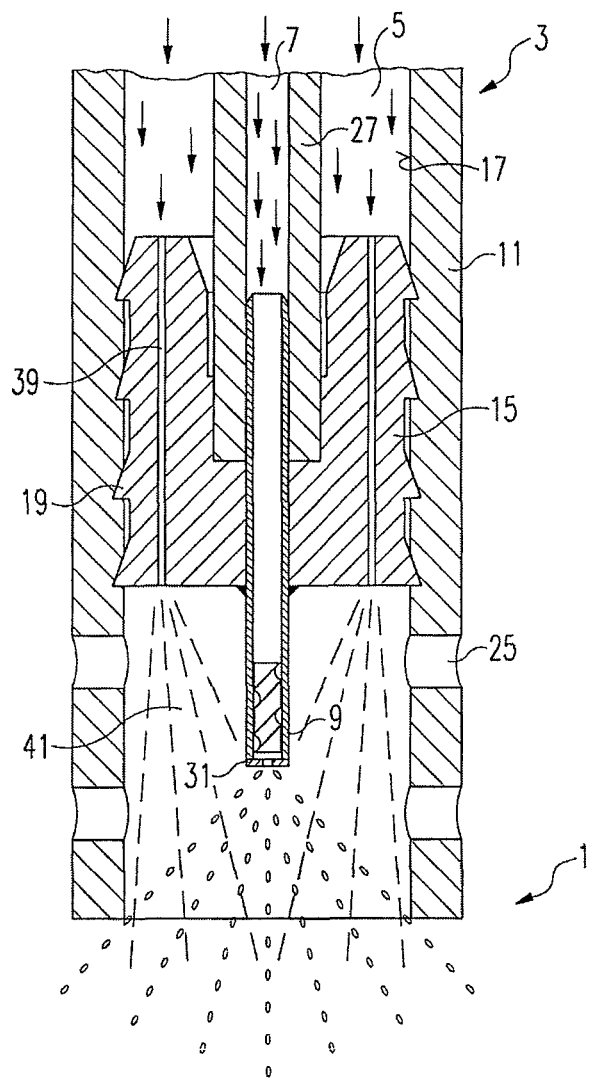
FIG. 2 is a schematic sectional view of a second embodiment of an anti-carbonization device.

FIG. 2 shows a schematic sectional view of a second embodiment of an anti-carbonization device 1 disclosed herein. The same parts are designated by the same reference numerals, where reference is made to the description for FIG. 1, to avoid repetition.

The surgical instrument 3 according to FIG. 2 again has a gas supply channel 5 and an oxidizing agent supply channel 7, which are arranged in the hose 11. In accordance with the embodiment shown in FIG. 1, a fixing sleeve 15 is provided and is arranged coaxially in the hose 11 and is secured through suitable locking projections 19 to the inner wall 17 of the hose 11. The hose 11 here too has lateral openings 25 to avoid a gas embolism.

The electrode tip 9 is further substantially centrally mounted in the fixing sleeve 15 and is connected to the pipe 97, which serves as an oxidizing agent supply channel 7. The electrode tip 9 is hollow and quasi serves as an extension of the oxidizing agent supply channel 7. The distal end of the electrode tip 9 in the embodiment according to FIG. 2 is also a nozzle with a suitable diameter and a suitable shape, so that the oxidizing agent passed through the oxidizing agent supply channel 7 is atomized upon exiting the channel.

In contrast to the embodiment shown in FIG. 1, the two-substance nozzle in FIG. 2, which is formed by the gas supply channel 5 and the oxidizing agent supply channel 7, is an external mixing one. The gas and the oxidizing agent are thus not fed to a common mixing chamber and then atomized; instead, the gas and the oxidizing agent are passed outwards in two separate channels and form the gas-oxidizing agent mixture only after exiting their respective supply channels 5 and 7.

For this purpose, at least one axial through-hole 39 is provided in the fixing sleeve 15 that connects the gas supply line 5 to a discharge region 41, into which the electrode tip 9 projects out of the fixing sleeve 15. Two through-holes 39 are recognizable in the sectional view in FIG. 2. It is also conceivable, however, to provide an annular space or for the fixing sleeve 15 to be in two parts, so that the gas passes through the annular space into the discharge region 41.

The gas-oxidizing agent mixture is therefore provided only in the discharge region 41 and not already in the oxidizing agent supply channel 7 according to FIG. 1. It is further possible for the gas and the oxidizing agent to interact in the discharge region 41 at the distal end 31 of the electrode tip 9 such that, upon collision of the gas and the oxidizing agent, atomization of the oxidizing agent results. An atomization nozzle is not necessary.

The oxidizing agent may also be liquid or gaseous with the embodiment according to FIG. 2. For example, it is conceivable to pass the oxidizing agent already in gaseous form through the oxidizing agent supply channel 7. The oxidizing agent in the discharge region 41, however, is preferably in the form of an aerosol. To generate an aerosol, the surgical instrument 3 preferably has an evaporator or heater. Further, an aerosol can be generated by an ultrasound generation device. It is also conceivable, however, to use a baffle surface against which the oxidizing agent rebounds and is atomized.

Figure 3:
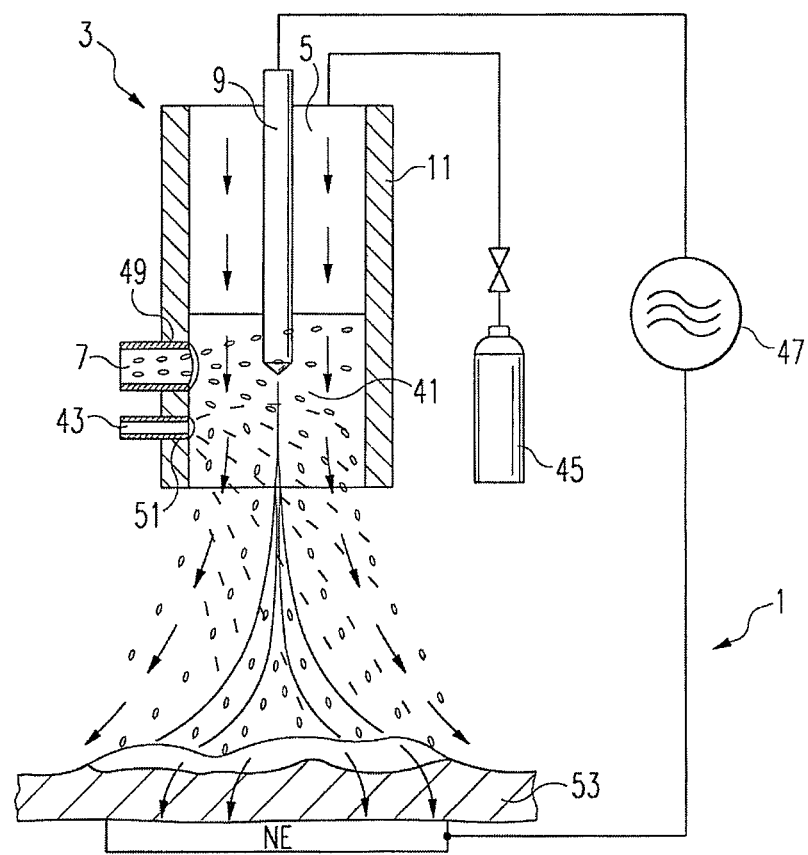
FIG. 3 is a schematic sectional view of a third embodiment of an anti-carbonization device.

FIG. 3 shows a schematic sectional view of a third embodiment of an anti-carbonization device 1 disclosed herein. The same parts are designated by the same reference numerals, where reference is made to the description for the preceding figures, to avoid repetition.

The anti-carbonization device 1 shown in FIG. 3 has a surgical instrument 3 for carrying out a plasma coagulation, which comprises a gas supply channel 5 and an oxidizing agent supply channel 7 that form a two-substance nozzle. Furthermore, an electrode tip 9 is provided in the hose 11.

In addition, a third supply channel 43 is provided, through which nanoparticles can optionally be passed to the gas-oxidizing agent mixture. The nanoparticles can attach themselves to a tissue surface 53 and support the desired therapeutic effect.

The gas supply channel 5 is formed as disclosed above for the two embodiments shown in FIGS. 1 and 2 mainly through the hose 11, which is connected to a suitable gas source 45. The electrode tip 9 is arranged in the hose 11, and is connected to a HF source 47, around which the gas flows.

The oxidizing agent supply channel 7 is connected via a lateral opening 49 to the hose 11, so that the oxidizing agent can pass through the opening 49 into the discharge region 41 where it encounters the gas from the gas supply channel 5, so that the gas-oxidizing agent mixture is provided in the discharge region 41. The same also applies for the third supply channel 43. Nanoparticles can thus pass through a corresponding opening 51 into the discharge region 41 where they form a mixture with the oxidizing agent and the gas.

The opening 49 is preferably formed so that liquid oxidizing agent is atomized when it leaves the oxidizing agent supply channel 7 so that an aerosol comprising oxidizing agent droplets and the gas is present in the discharge region 41. It is also conceivable, however, to evaporate the oxidizing agent prior to its introduction into the oxidizing agent supply channel 7 using an evaporator and to supply an oxidizing agent vapor to the discharge region 41. It is also conceivable, however, to evaporate the oxidizing agent only in the discharge region 41.

Furthermore, an atomization of liquid oxidizing agent can be brought about firstly in the discharge region 41, for example through a baffle plate or through ultrasound.

Figure 4:
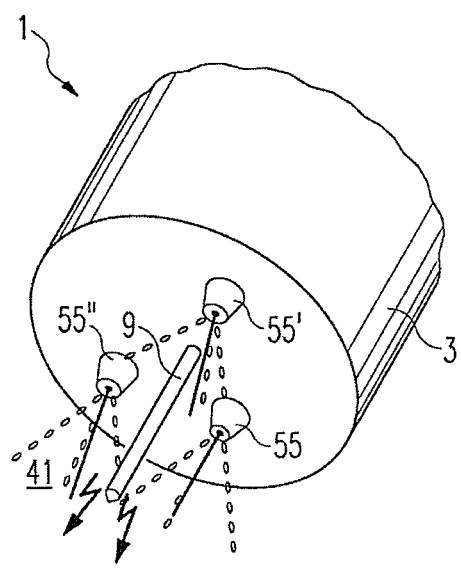
FIG. 4 is a perspective view of a fourth embodiment of an anti-carbonization device.

FIG. 4 shows a perspective view of a fourth embodiment of an anti-carbonization device 1 disclosed herein. The same parts are designated by the same reference numerals, where reference is made to the description of the preceding figures, to avoid repetition.

FIG. 4 shows a centrally-disposed rod-shaped electrode tip 9 that projects out of the surgical instrument 3. Three two-substance nozzles, not shown in detail, are provided around the electrode tip 9, and have three outlet openings 55, 55' and 55". The surgical instrument may, for example, be formed as shown in FIG. 1 or FIG. 2, where instead of one two-substance nozzle a total of three internal-mixing or external-mixing two-substance nozzles are provided. The gas-oxidizing agent mixture or oxidizing agent then flows out of the outlet openings 55, 55' and 55". The outlet openings 55, 55' and 55" are preferably formed such that the gas-oxidizing agent mixture is atomized so that it is in the form of an aerosol in the discharge region 41.

Figure 5:
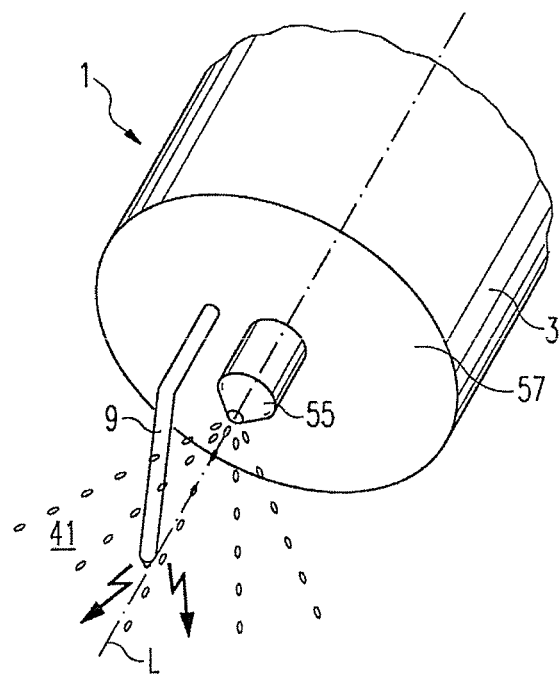
FIG. 5 is a perspective view of a fifth embodiment of an anti-carbonization device.

FIG. 5 shows a perspective view of a fifth embodiment of an anti-carbonization device 1. The same parts are designated by the same reference numerals, where reference is made to the description of the preceding figures, to avoid repetition.

In FIG. 5 the electrode tip 9 is arranged eccentrically with respect to the surgical instrument 3 and extends into the discharge region 41. An outlet opening 55 of a two-substance nozzle, not shown in detail, is arranged centrally with respect to the surgical instrument 3. With this embodiment too, the two-substance nozzle may be of internal mixing or external mixing design.

FIG. 5 clearly shows that the electrode tip 9 is formed such that it projects from its eccentric discharge position into the region of a longitudinal axis L of the outlet opening 55. The base body 57 of the surgical instrument 3 is formed, moreover, preferably so that it is electrically insulating.

Figure 6:
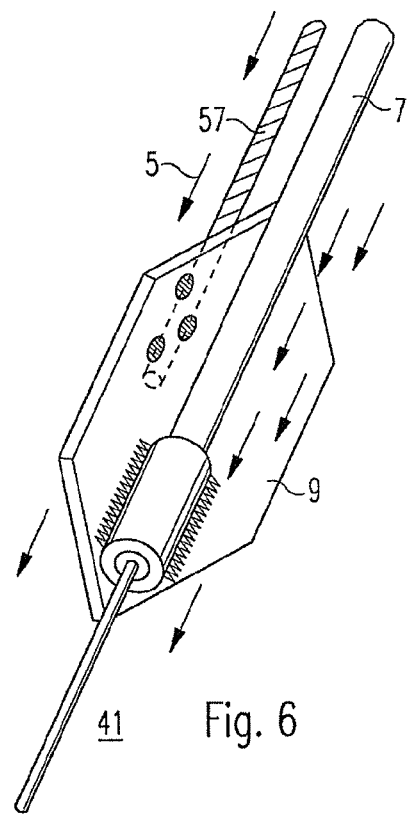
FIG. 6 is a schematic view of a surgical instrument with an electrode and a two-substance nozzle.

FIG. 6 shows a schematic view of a surgical instrument 3 with an electrode and a two-substance nozzle. The same parts are designated by the same reference numerals, where reference is made to the description of the preceding figures, to avoid repetition.

The two-substance nozzle in FIG. 6 has external mixing. The electrode tip 9 is further formed as a metal plate with an electrical lead 57, where the gas flows past the metal plate.

The oxidizing agent supply channel 7 is secured to the electrode tip 9, i.e., to the metal plate, and generates a laminar jet, the oxidizing agent is a liquid. The gas-oxidizing agent mixture for generation of a gas-oxidizing agent plasma is then made available in the discharge region 41.

Figure 7:
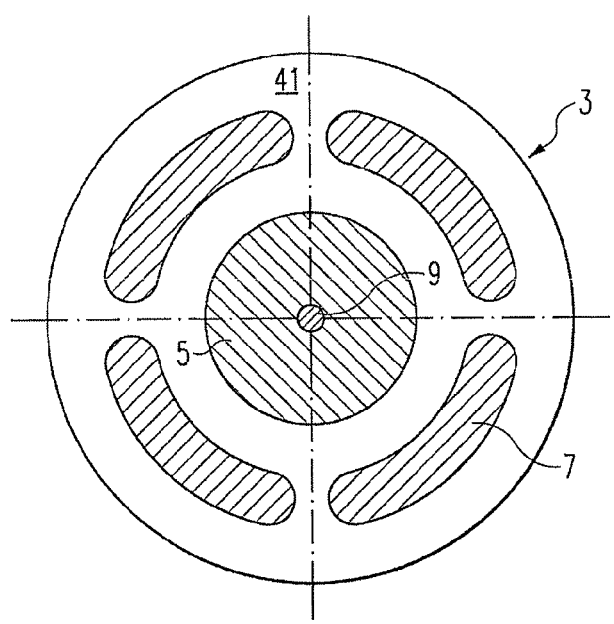
FIG. 7 is a top view of a discharge region of a surgical instrument.

FIG. 7 shows a top view of a discharge region 41 of a surgical instrument 3. The same parts are designated by the same reference numerals, where reference is made to the description of the preceding figures, to avoid repetition.

FIG. 7 shows an external-mixing two-substance nozzle system, where the electrode tip 9 is arranged centrally and is enveloped by the gas supply channel 5. Four kidney-shaped oxidizing agent supply channels 7 are provided coaxially to the gas supply channel 5.

Figure 8:
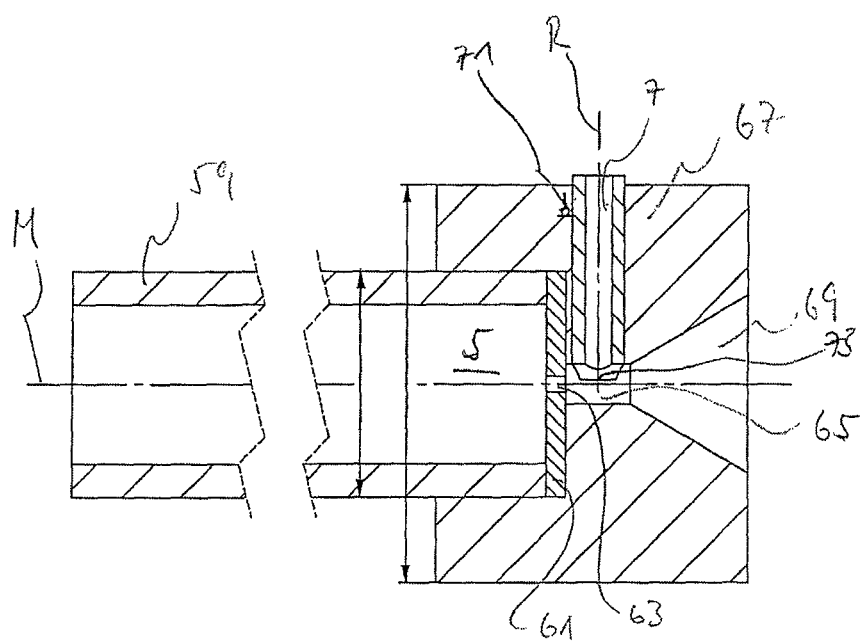
FIG. 8 is a schematic sectional view of an embodiment of a surgical instrument with Venturi nozzle.

FIG. 8 shows a further embodiment of the invention in which a gas-oxidizing agent mixture/an aerosol-oxidizing agent plasma or gas-oxidizing agent plasma is generated by the principle of a (gas) jet pump, i.e., by the Venturi principle, wherein a negative pressure is generated through constriction of a supply channel. Such jet pumps are generally known. The basic principle of such pumps is that a liquid or gaseous jet exits a nozzle at high speed and carries with it liquid, gas or solid from the surrounding area and accelerates it.

In accordance with the present disclosure a gas supply channel 5 that has a wall 59 may be provided for a gas, in particular argon. The gas preferably flows through an aperture 61 arranged at the distal end of the gas supply channel 5 and in particular through a central discharge opening 63 in the aperture 61 into a cylindrical mixing region 65 of a top section 67, where the top section 67 is arranged at the distal end of the gas supply channel 5. The top section 67 may be formed integrally with the gas supply channel 5 or with its wall 59. It is also conceivable, however, for the top section 67 to be formed as a separate part and to be connected to the gas supply channel 5 in a suitable manner, in particular by gluing, soldering or the like. A frustoconical atomization region 69 adjoins the cylindrical mixing area 65 and is similarly centrally formed in the top section 67.

FIG. 8 clearly shows that the gas supply channel 5, the opening 63, the mixing region 65 and the atomization area 69 extend along a central axis M, and are arranged substantially symmetrically to it in sequence. An oxidizing agent supply pipe 71, in which an oxidizing agent supply channel 7 is provided, extends along a radial axis R transversely to the central axis M. The oxidizing agent supply pipe 71 is connected to a source of oxidizing agent, not shown. The oxidizing agent supply pipe 71 is connected to a source of oxidizing agent, the top section 67 that extends radially along the axis R or is integral with it and opens with its open end section 73 into the distal cylindrical mixing region 65.

The principle of function of the embodiment according to FIG. 8 is as follows: at the bottleneck in the cylindrical mixing region 65 behind the opening 63, the static pressure of the gas for energy conservation reasons has to be lower than in the non-constricted parts of the device. As a result of the gas flow in the gas supply channel 5 or the mixing region 65, an oxidizing agent to be atomized, in particular water, is aspirated from the oxidizing agent supply channel 7 by the negative pressure in the mixing region 65 and is entrained in the gas stream. It is therefore an (external mixing) self-aspirating two-substance nozzle/a Venturi nozzle, which has the advantage that a separate pump is not required for the supply of the oxidizing agent. Rather, the oxidizing agent is drawn into the mixing region 65 automatically through the gas flow. The gas supply channel 5 and the oxidizing agent supply channel 7 in this embodiment of the invention are therefore advantageously formed as a self-aspirating two-substance atomization device or as an (external-mixing) Venturi nozzle.

The desired gas-oxidizing agent mixture, in particular in the form of an aerosol, is then present in the atomization region 69 commencing from the mixing region 65 and a gas-oxidizing agent plasma is ignited by a suitable electrode.

Overall, the present invention discloses an anti-carbonization device 1, which provides in an advantageous manner a gas-oxidizing agent mixture for producing a gas-oxidizing agent plasma by means of a surgical instrument 3.

The gas-oxidizing agent mixture has at least two components, where one component is a gas, in particular a noble gas such as argon or helium, and the other component is an oxidizing agent for carbon. The oxidizing agent may consist of solid or liquid suspended particles, for example, small water droplets, which are present as water mist. The liquid oxidizing agent is thereby atomized very finely so that its surface area is greatly enlarged. In this way, the evaporation point is substantially lowered, so that in addition to the liquid oxidizing agent droplets a significant proportion is present as an oxidizing agent vapor. The high-frequency alternating current can also ionize oxidizing agent molecules, in particular water molecules, in the gas phase to form a water vapor-plasma mixture.

The above description makes it clear that the gas-oxidizing agent mixture is preferably an aerosol, which therefore has gaseous particles and finely-atomized oxidizing agent droplets. The aerosol plasma enables carbonization of the tissue to be largely avoided, where the oxidizing agent mist, in particular the water mist, i.e., the $H_2O$ droplets, at the same time acts as an oxidizing agent for carbon, as a coolant for the tissue surface and as plasma medium.

Furthermore, the significant reduction in carbonization is directly linked to the emission quantities of carbon black and gases contained in smoke such as $CO_2$, $CO$, $NO$, $NO_x$ and $SO_x$, as well as organic and biochemical molecules, so that the proposed device and the corresponding method lead to a significant reduction in the above-mentioned emissions and thus reduce the exposure risks of the patient and surgical personnel.

Moreover, the proposed anti-carbonization device enables a homogeneous, tissue-conserving coagulation and devitalization, with the aim of deploying the method in a tissue-preserving manner preferably in the field of oncosurgery, but also in other medical disciplines, for example for tumor ablation, especially in thin-wall and nerve-sensitive structures, in neurosurgery, urology and as an adhesion-reducing surgical method in gynecology and visceral surgery, both open surgery and endoscopic (rigid and flexible).

Furthermore, at least one two-substance nozzle can be provided, which can be of internal-mixing or external-mixing design. In addition, the surgical instrument 3 can have a suitable mechanism, for example an evaporator, an ultrasound generator or a baffle plate, to generate an oxidizing agent aerosol/a gas-oxidizing agent aerosol. The oxidizing agent can be atomized either before or after being mixed with the gas. The sole decisive aspect is that the gas contains liquid oxidizing agent droplets to bring about the advantages described above.

Embodiments of the invention thus effectively reduce carbonization and the development of carbon black and smoke. Furthermore, a more uniform distribution of the plasma energy is obtained on the tissue surface.

The above advantages are also achieved by a method according to an embodiment of the invention, which provides a gas-oxidizing agent mixture for the performance of a plasma coagulation. The same applies with regard to the use of an anti-carbonization device 1 to prevent carbonization of the tissue.

The invention claimed is:

1. An anti-carbonization device for preventing carbonization of tissue upon plasma coagulation,
said anti-carbonization device for receiving an oxidizing agent and a gas, and for providing a gas-oxidizing agent mixture for generating a gas-oxidizing agent plasma, the anti-carbonization device comprising at least one two-substance atomization device to feed the oxidizing agent.

2. The anti-carbonization device according to claim 1, wherein the oxidizing agent is a liquid.

3. The anti-carbonization device according to claim 1, wherein the oxidizing agent is gaseous.

4. The anti-carbonization device according to claim 1, wherein the oxidizing agent is an aerosol.

5. The anti-carbonization device according to claim 1, wherein the oxidizing agent is water.

6. The anti-carbonization device according to claim 1, wherein the gas is an inert gas.

7. The anti-carbonization device according to claim 6, wherein the gas is argon.

8. The anti-carbonization device according to claim 1, wherein the at least one two-substance atomization device is an internal-mixing device.

9. The anti-carbonization device according to claim 1, wherein the at least one two-substance atomization device is an external-mixing device.

10. The anti-carbonization device according to claim 1, wherein the at least one two-substance atomization device is a self-aspirating two-substance atomization device.

* * * * *